United States Patent [19]

Kao et al.

[11] Patent Number: 5,378,836
[45] Date of Patent: Jan. 3, 1995

[54] RAPAMYCIN OXIMES AND HYDRAZONES

[75] Inventors: Wenling Kao, Paoli, Pa.; Robert L. Vogel, Stratford, N.J.; Magid A. Abou-Gharbia, Glen Mills, Pa.; Craig E. Caufield, Princeton Junction, N.J.

[73] Assignee: American Home Products Corporation, Madison, N.J.

[21] Appl. No.: 134,224

[22] Filed: Oct. 8, 1993

[51] Int. Cl.$^6$ ............... A61K 31/395; C07D 491/06
[52] U.S. Cl. .................................. 540/456; 540/452
[58] Field of Search ............... 540/456, 452; 514/291, 514/63

[56] References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 4,316,885 | 2/1982 | Rakhit | 540/456 |
| 4,375,464 | 3/1993 | Sehgal et al. | 540/456 |
| 4,401,653 | 8/1983 | Eng | 540/456 |
| 4,650,803 | 3/1987 | Stella et al. | 540/456 |
| 4,885,171 | 12/1989 | Surendra et al. | 540/456 |
| 5,023,262 | 6/1991 | Caufield et al. | 540/456 |
| 5,023,263 | 6/1991 | Von Burg | 540/456 |
| 5,023,264 | 6/1991 | Caufield et al. | 540/456 |
| 5,078,999 | 1/1992 | Warner et al. | 540/456 |
| 5,080,899 | 1/1992 | Sturm et al. | 540/456 |
| 5,091,389 | 2/1992 | Ondeyka et al. | 540/456 |
| 5,100,883 | 3/1992 | Schiehser | 540/456 |
| 5,100,899 | 3/1992 | Calne | 540/456 |
| 5,102,876 | 4/1992 | Caufield | 540/456 |
| 5,118,677 | 6/1992 | Caufield | 540/456 |
| 5,118,678 | 6/1992 | Kao et al. | 540/456 |
| 5,120,726 | 6/1992 | Failli et al. | 540/456 |
| 5,120,842 | 6/1992 | Failli et al. | 540/456 |
| 5,130,307 | 7/1992 | Failli et al. | 540/456 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 540/456 |
| 5,177,203 | 1/1993 | Failli et al. | 540/456 |
| 5,194,447 | 3/1993 | Kao | 540/456 |
| 5,221,670 | 6/1993 | Caufield | 540/456 |
| 5,233,036 | 8/1993 | Hughes | 540/456 |

FOREIGN PATENT DOCUMENTS

507555A1  7/1992  European Pat. Off. ............ 540/456

OTHER PUBLICATIONS

Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11(pt. 2):197 (1992).
Stepkowski, S. M., Transplantation Proc. 23:507 (1991).
Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Kao et al., Commonly owned U.S. patent application Ser. No. 08/054,655 Filed: Apr. 23, 1993 now refered to U.S. Pat. No. 5,302,384 issued Apr. 12, 1994.

*Primary Examiner*—Robert T. Bond
*Attorney, Agent, or Firm*—Arnold S. Milowsky

[57] ABSTRACT

A compound of the structure

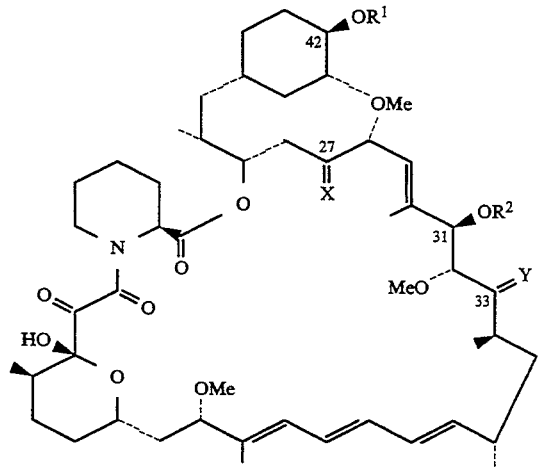

wherein $R^1$ and $R^2$ are each, independently, hydrogen, —CONH$_a$—{{(CR$^3$R$^4$)$_m$(—A—(CR$^5$R$^6$)$_n$)$_p$}$_q$—B}$_r$; —SO$_2$R$^7$; —SO$_3$H; —CHR$^8$O(CH$_2$)$_t$R$^9$; or

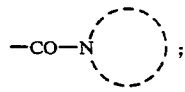

$R^3$, $R^4$, $R^5$, $R^6$, and B are each, independently, hydrogen, alkyl, alkenyl, alkynyl, hydroxyalkyl, alkoxyalkyl, alkylthioalkyl, alkylaminoalkyl, dialkylaminoalkyl, arylalkyl, cycloalkyl, —OR$^{10}$, —SR$^{10}$, halogen, —CN, —NO$_2$, —CF$_3$, —COR$^{10}$, —CO$_2$R$^{10}$, —CONHR$^{10}$, —SO$_2$R$^{10}$, —OSO$_3$R$^{10}$, —NR$^{10}$R$^{11}$, —NHCOR$^{10}$, —NHSO$_2$R$^{10}$, or Ar;

X is =NOR$^{12}$ or =NNR$^{12}$R$^{13}$;

Y is O, =NOR$^{12}$, or =NNR$^{12}$R$^{13}$;

$R^7$, $R^{12}$, and $R^{13}$ are each, independently, hydrogen, alkyl, alkenyl, alkynyl, arylalkyl;

$R^8$, $R^9$, $R^{10}$, and $R^{11}$ are each, independently, hydrogen, alkyl, arylalkyl, alkenyl, alkynyl, hydroxyalkyl, alkoxyalkyl, alkylthioalkyl, alkylaminoalkyl, dialkylaminoalkyl, cycloalkyl, or Ar;

A is —CH$_2$—, —NR$^8$—, —O—, —S—, —SO—, —SO$_2$—, —PR$^8$—, —CO—, —NHCO—, —NHSO—, or —P(O)(R$^8$)—;

Ar is aryl which may be optionally mono-, di-, or tri- substituted;

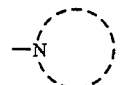

is a nitrogen containing heterocycle that may be saturated, unsaturated, or partially unsaturated, and may be optionally mono-, di-, or tri- substituted;

a=0–1;
m=0–6;
n=0–6;
p=0–1;
q=0–1;
r=1–2; and
t=1–4;

wherein $R^3$, $R^4$, $R^5$, $R^6$, A, B, m, n, p, and q are independent in each of the —CON—{{(CR$^3$R$^4$)$_m$(—A—(CR$^5$R$^6$)$_n$)$_p$}$_q$—B}$_r$ subunits when r=2;

with the proviso that $R^1$ and $R^2$ are not both hydrogen, and further provided that if r=2, then a=0, and if r=1, then a=1;

or a pharmaceutically acceptable salt thereof which is useful as an immunosuppressive, antiinflammatory, antifungal, antiproliferative, and antitumor agent.

21 Claims, No Drawings

RAPAMYCIN OXIMES AND HYDRAZONES

BACKGROUND OF THE INVENTION

This invention relates to oximes and hydrazones of rapamycin and a method for using them for inducing immunosuppression, and in the treatment of transplantation rejection, host vs. graft disease, autoimmune diseases, diseases of inflammation, adult T-cell leukemia/-lymphoma, solid tumors, fungal infections, and hyperproliferative vascular disorders.

Rapamycin is a macrocyclic trione antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Parent Application 532,862 A 1].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, anti-inflammatory, antifungal, and antitumor agents. U.S. Pat. No. 5,194,447 discloses sulfonyl carbamates useful as immunosuppressive, anti-inflammatory, antifungal, and antitumor agents. U.S. Pat. No. 5,177,203 discloses sulfonates of rapamycin useful as immunosuppressive, antiinflammatory, and antifungal, agents. U.S. Pat. No. 5,023,264 discloses oximes of rapamycin useful as immunosuppressive, antiinflammatory, and antifungal agents. U.S. Pat. No. 5,120,726 discloses hydrazones of rapamycin useful as immunosuppressive, antiinflammatory, and antifungal agents. U.S. Pat. No. 5,151,413 discloses acetals of rapamycin useful as immunosuppressant and antifungal agents.

DESCRIPTION OF THE INVENTION

This invention provides derivatives of rapamycin which are useful as immunosuppressive, antiinflammatory, antifungal, antiproliferative, and antitumor agents having the structure

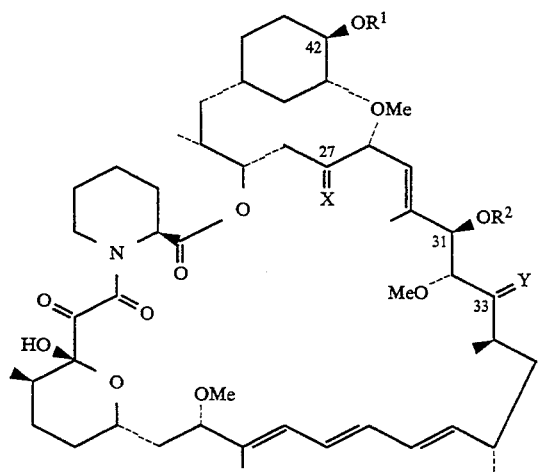

wherein $R^1$ and $R^2$ are each, independently, hydrogen, $-CONH_a-\{\{(CR^3R^4)_m(-A-(CR^5R^6)_n)_p\}_q-B\}_r$; $-SO_2R^7$; $-SO_3H$; $-CHR^8O(CH_2)_tR^9$; or

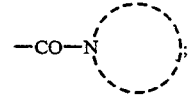

$R^3$, $R^4$, $R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-OR^{10}$, $-SR^{10}$, halogen, $-CN$, $-NO_2$, $-CF_3$, $-COR^{10}$, $-CO_2R^{10}$, $-CONHR^{10}$, $-SO_2R^{10}$, $-OSO_3R^{10}$, $-NR^{10}R^{11}$, $-NHCOR^{10}$, $-NHSO_2R^{10}$, or Ar;

X is $=NOR^{12}$ or $=NNR^{12}R^{13}$;

Y is O, $=NOR^{12}$, or $=NNR^{12}R^{13}$;

$R^7$, $R^{12}$, and $R^{13}$ are each, independently, hydrogen, alkyl of 1–6 carbon atoms, alkenyl of 2–7 carbon atoms, alkynyl of 2–7 carbon atoms, arylalkyl of 7–10 carbon atoms, or Ar;

$R^8$, $R^9$, $R^{10}$, and $R^{11}$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is $-CH_2-$, $-NR^{10}-$, $-O-$, $-S-$, $-SO-$, $-SO_2-$, $-PR^{10}-$, $-CO-$, $-NHCO-$, $-NHSO-$, or $-P(O)(R^{10})-$;

Ar is aryl which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

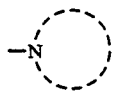

is a nitrogen containing heterocycle that may be saturated, unsaturated, or partially unsaturated, and may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;
a=0–1;
m=0–6;
n=0–6;
p=0–1;
q=0–1;
r=1–2; and
t=0–4;
wherein $R^3$, $R^4$, $R^5$, $R^6$, A, B, m, n, p, and q are independent in each of the —CON—{{(CR$^3$R$^4$)$_m$(—A—(CR$^5$R$^6$)$_n$)$_p$}$_q$—B}$_r$ subunits when r=2;
with the proviso that $R^1$ and $R^2$ are not both hydrogen, and further provided that if r=2, then a=0, and if r=1, then a=1;
or a pharmaceutically acceptable salt thereof.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the aryl moiety of the Ar group or of the arylalkyl group is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, benzopyranyl, benz[b]thiophenolyl, benzimidazolyl, benzthiazolyl, benzodioxolyl, piperidyl, morpholinyl, piperazinyl, tetrahydrofuranyl, or pyrrolidinyl group which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H. It is more preferred that the aryl moiety is a phenyl, naphthyl, or pyridyl group that may be optionally substituted as described above.

It is preferred that

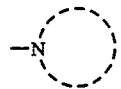

is a pyridyl, pyrazinyl, piperidinyl, morpholinyl, piperazinyl, pyrrolidinyl, thiazolyl, pyrimidinyl, isoxazolyl, pyrrolidinyl, or imidazolyl group that may be optionally substituted as described above.

Of the compounds of this invention, preferred members are those in which X is =NOR$^{12}$ and Y is O; those in which X is =NOR$^{12}$, Y is O, $R^1$ is —CONH$_a$—{{(CR$^3$R$^4$)$_m$(—A—(CR$^5$R$^6$)$_n$)$_p$}$_q$—B}$_r$, r=1, a=1, and $R^2$ is hydrogen; those in which X is =NOR$^{12}$, Y is O, $R^1$ is —CONH$_a$—{{(CR$^3$R$^4$)$_m$(—A—(CR$^5$R$^6$)$_n$)$_p$}$_q$—B}$_r$, r=1, a=1, $R^2$ is H, and q=0; those in which X is =NOR$^{12}$, Y is O, $R^1$ is —CONH$_a$—{{(CR$^3$R$^4$)$_m$(—A—(CR$^5$R$^6$)$_n$)$_p$}$_q$—B}$_r$, r=1, a=1, $R^2$ is H, q=0, and B is Ar or OR$^{10}$; those in which X is =NOR$^{12}$, y is O, $R^1$ is —CONH$_a$—{{(CR$^3$R$^4$)$_m$(—A—(CR$^5$R$^6$)$_n$)$_p$}$_q$—B}$_r$, r=1, a=1, $R^2$ is H, q=0, B is Ar or OR$^{10}$, and Ar is phenyl or pyridyl; those in which X is =NOR$^{12}$, Y is O, $R^1$ is —SO$_2$R$^7$, and $R^2$ is hydrogen; and those in which X is =NOR$^{10}$, Y is O, $R^1$ is —SO$_2$R$^7$, $R^2$ is hydrogen, and $R^7$ is Ar.

When either X or Y is NOR$^{12}$, the 27- and/or 33-oxime can exist in both the E and the Z forms; this disclosure covers both of these forms.

For the compounds of this invention in which the 31- and/or 42-hydroxyl groups of rapamycin has been carbamylated, the carbamylation of one or both of these hydroxyl groups can be accomplished by reacting one or both of the hydroxyl groups with an appropriately substituted isocyanate according to the method described in U.S. Pat. No. 5,118,678, which is hereby incorporated by reference. Alternatively, carbamylation of the 42-hydroxyl group or bis-carbamylation of the 31-and 42-hydroxyl groups can be accomplished by reacting either the 42- or the 31- and 42-hydroxyl groups with a reagent to create a suitable leaving group at the 42- and or 31-and 42-hydroxyl groups, such as p-nitrophenylchloroformate to give the 42- or the 31-and 42-carbonate of rapamycin. The carbonate can then be reacted with a suitable amine to give the desired 42-carbamate or 31,42-biscarbamate. This methodology can also be used to prepare 31-carbamylated compounds by first protecting the 42-hydroxyl group with a suitable protecting group, such as a silyl ether, as described in U.S. Pat. No. 5,118,678 followed by reaction of the 31-hydroxyl group to form a carbonate, subsequent reaction with an amine, and then cleavage of the 42-protecting group. Compounds in which the 42- and 31-hydroxyl groups contain different carbamate groups can be prepared using either the isocyanate or carbonate route either by first forming a carbamate at the 42-position and then reacting the 31-hydroxyl group with a different isocyanate or with a different amine following formation of the 31-carbonate.

For the compounds of this invention in which the 31- and/or 42-hydroxyl groups of rapamycin have been converted to a sulfonyl carbamate, the sulfonyl carbamylation can be accomplished according to the methodology described in U.S. Pat. No. 5,194,447, which is hereby incorporated by reference. Selectivity between the 31- and 42-positions can be obtained as described above.

For the compounds of this invention in which the 31- and/or 42-hydroxyl groups of rapamycin have been converted to a sulfonate, the sulfonation can be accomplished according to the methodology described in U.S. Pat. No. 5,177,203, which is hereby incorporated by reference. Selectivity between the 31- and 42-positions can be obtained as described above.

For the compounds of this invention in which the 31- and/or 42-hydroxyl groups of rapamycin have been converted to an acetal or ketal, the acetal or ketal formation can be accomplished according to the methology described in U.S. Pat. No. 5,151,413, which is hereby incorporated by reference. Selectivity between the 31- and 42-positions can be obtained as described above.

Using the methodology described above, combinations of carbamates and sulfonates can be obtained on the 31- and 42-positions, and vice versa by reacting the 42-hydroxyl with the first group and then the 31-hydroxyl with a different group. Alternatively, the 42-position can be protected first, as described above, followed by reaction at the 31-position, cleavage of the 42-protected hydroxyl group and then reaction of the 42-hydroxyl group with a second electrophile.

For the compounds of this invention in which the 27- or 27- and 33-positions have been converted to an oxime, the oximation reaction can be accomplished according to the methodology described in U.S. Pat. No. 5,023,264, which is hereby incorporated by reference. In oximating rapamycin, the 27-position is more reactive than the 33-position and can therefore be selectively oximated over the 33-position.

For the compounds of this invention in which the 27- or 27- and 33-positions have been converted to, a hydrazone, the hydrazonation reaction can be accomplished according to the methodology described in U.S. Pat. No. 5,120,726, which is hereby incorporated by reference. In converting rapamycin to the corresponding hydrazones, the 27-position is more reactive than the 33-position and can therefore be selectively converted to a hydrazone over the 33-position.

By taking advantage of the reactivity difference between the 27- and 33-ketones of rapamycin, mixed oxime/hydrazone derivatives of rapamycin can be prepared. The 27-ketone can first be oximated followed by conversion of the 33-ketone to a hydrazone, or vice versa.

In preparing the compounds of this invention, there is no preference in whether the ketones (27- and/or 33-) are converted to oximes or hydrazones first or whether the hydroxyl groups (42- and/or 31-) are converted to carbamates, sulfonyl carbamates, sulfonates, acetals, or ketals first.

The amines, isocyanates, acetal and ketal forming reagants, hydroxylamines, and hydrazines used to prepare the compounds of the invention are commercially available or can be prepared by methods that are disclosed in the literature.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxyrapamycin [U.S. Pat. No. 5,102,876]. The disclosures in the above cited U.S. patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 0.4–9.8 nM. The results obtained are provided as an $IC_{50}$ and as the percent inhibition of T-cell proliferation at 0.1 $\mu$M.

Representative compounds of this invention were also evaluated in an in vivo test procedure designed to determine the survival time of pinch skin graft from male BAB/c donors transplanted to male C3H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 12.0±1.7 days was obtained for rapamycin at 4 mg/kg.

The following table summarizes the results of representative compounds of this invention in these two standard test procedures.

TABLE 1

| EVALUATION OF IMMUNOSUPPRESSIVE ACTIVITY | | | |
|---|---|---|---|
| | LAF | | Skin Graft |
| Compound | $IC_{50}$ (nM) | % Inhib.+ | (days ± SD) |
| Example 2 | 0.6 | 94 | 8.0 ± 0.6 |
| Example 4 | 17.8 | 89 | |
| Example 6 | | 71 | 9.8 ± 0.4 |

TABLE 1-continued

| EVALUATION OF IMMUNOSUPPRESSIVE ACTIVITY | | | |
|---|---|---|---|
| | LAF | | Skin Graft |
| Compound | IC$_{50}$ (nM) | % Inhib.+ | (days ± SD) |
| Example 8 | 13.9 | 87 | 7.0 ± 0.0 |
| Example 10 | 300 | 20 | |
| Example 11 | 255 | 17 | |
| Example 12 | 210 | 30 | |
| Example 13 | 580 | 14 | |
| Example 14 | >1000 | 20 | |
| Example 16 | 100 | 47 | |
| Example 17 | 30 | 73 | 7.8 ± 0.4 |
| Example 18 | 279 | 18 | |

+Percent inhibition of T-cell proliferation at 0.1 µM.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. The results; obtained for representative compounds of this invention in preventing skin graft rejection further demonstrates their utility as immunosuppressive agents.

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogen sled hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

Rapamycin 42-ester with 2-(pyridin-2-yl)-ethyl carbamic acid

A solution of 210 mg rapamycin 42-p-nitrophenyl carbonate in 8 ml dichloromethane was treated at −10° under $N_2$ with 122 mg 2-(2-amino-ethyl)-pyridine in 1 ml dichloromethane. The reaction mixture was stirred at 0° under $N_2$ for one hour, diluted with 200 ml dichloromethane, washed with ice-cold 1N HCl, water, and dried with $MgSO_4$. The solvent was evaporated and the residue chromatographed on silica gel. Elution with ethyl acetate/n-hexane (4/1) afforded 70 mg of the title product as a white solid, mp 95°–98°.

IR (KBr): 3400 (OH and NH), 1720 (lactone and ketone C=O), 1645 (amide C=O), 1450, 1250, 1090, 1100 and 990 cm$^{-1}$.

$^1$H NMR (CDCl$_3$, 400 MHz): δ 8.52 (d, J=12 cps, 1H, proton c), 7.59 (t, 1H, proton b), 7.12 (m, 2H, protons a), 3.32, 3.31 and 3.12 (each s, 3H, OCH$_3$), 3.58 (t, 2H, protons e), 2.97 (t, 2H, protons d) ppm. MS (neg. ion FAB): 1061 (M−), 590, 469.

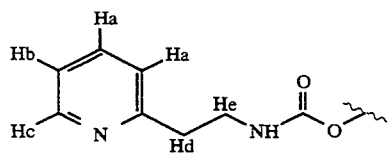

EXAMPLE 2

Rapamycin 27-oxime, 42-ester with 2-(pyridin-2-yl)-ethyl-carbamic acid

A solution of 550 mg rapamycin 42-ester with 2-(pyridin-2-yl)-ethyl carbamic acid in 15 ml methanol was treated at room temperature under $N_2$ with 180 mg sodium acetate and 150 mg hydroxylamine hydrochloride. The mixture was stirred at room temperature under $N_2$ for 4 hours diluted with 100 ml water and extracted with ethyl acetate (4×50 ml). The ethyl acetate extract was washed, dried over $MgSO_4$ and evaporated to dryness. The residue was chromatographed on silica gel. Elution with ethyl acetate/n-hexane=4/1 afforded 408 mg of the title compound as a white solid, mp 95°–98°.

IR (KBr): 3430 (OH and NH), 1730 (lactone and ketone C=O), 1645 (amide C=O), 1450, 1250, 1200, 1100, 980 cm$^{-1}$. $^1$H NMR (CDCl$_3$, 400 MHz): 8.50 (d, J=12 cps, 1H, proton c), 7.59 (t, 1H, proton b), 7.14 (m, 2H, protons a). 3.33 (d), 3.29 (s), 3.12 (d) (each 3H, —OCH$_3$), 3.57 (t, 2H, protons d), 2.99 (t, 2H, protons e) ppm.

MS (neg. ion FAB): 1076 (M−), 590. 297.

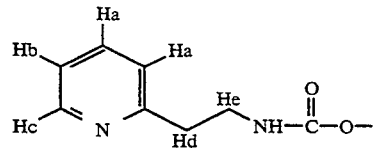

EXAMPLE 3

Rapamycin 42-ester with 2-hydroxyethyl carbamic acid

A solution of 270 mg rapamycin 42-p-nitrophenyl carbonate in 8 mL dichloromethane was treated at −10° C. under a nitrogen atmosphere with 61 mg ethanolamine in 0.5 mL dichloromethane. The yellow solution was stirred at 0° C. under a nitrogen atmosphere for 45 minutes. The reaction mixture was diluted with 120 mL dichloromethane, washed with 1N HCl, water, dried with MgSO$_4$ and evaporated. The residue was chromatographed on silica gel. Elution with ethyl acetate/n-hexane (2/1) afforded 85 mg of the title compound as a white foam, mp 100°–105°.

IR(KBr): 3430 (OH, NH), 1720 (lactone and ketone C=O)), 1640 (amide C=O), 1520, 1450, 1240, 1080, 985 and 760 cm$^{-1}$. $^1$H NMR (CDCl$_3$, 400 MHz): 3.70 (m, 2H, —CH$_2$—OH), 3.65 (m, 2H, —NH—CH$_2$), 3.38, 3.33, 3.14 (all s, 3H, —OCH$_3$) ppm. MS (neg ion FAB): 1000 (M−), 590, 408, 297.

EXAMPLE 4

Rapamycin 27-oxime, 42-ester with 2-hydroxyethyl carbamic acid

A solution of 360 mg rapamycin 42-ester with 2-hydroxyethyl carbamic acid in 10 ml methanol was treated at room temperature under $N_2$ with 120 mg sodium acetate and 100 mg hydroxylamine hydrochloride. The mixture was stirred at room temperature under nitrogen for 5 hours, diluted with 40 ml water and extracted with ethyl acetate (4×50 ml). The ethyl acetate extract was washed, dried over $MgSO_4$ and evaporated to dryness. The residue was chromatographed on silica gel. Elution with ethyl acetate/n-hexane=4/1 afforded 200 mg of the title compound as a white solid, mp 125°-128°.

IR (KBr): 3430 (OH and NH), 1730 (lactone and ketone C=O), 1640 (amide C=O), 1460, 1080, 990 cm$^{-1}$.

$^1$H NMR (CDCl$_3$, 400 MHz): 3.38, 3.31, 3.14 (each 3H, —OCH$_3$), 3.75 (t, 2H, —CH$_2$—OH), 3.37 (m, 2H, —CH$_2$—NH—) ppm.

MS (neg. ion FAB): 1015 (M−), 590,336, 167.

EXAMPLE 5

Rapamycin 27-oxime

Rapamycin 27-oxime was prepared according to the procedure of Example 6 in U.S. Pat. No. 5,023,264.

EXAMPLE 6

Rapamycin 27-oxime, 42-sulfate ester pyridine salt

A solution of 160 mg rapamycin 27-oxime in 1 ml pyridine was treated at 0° under N$_2$ with 81 mg sulfur trioxide pyridine, complex and stirred at room temperature under N$_2$ for 3 days. The suspension was evaporated under reduced pressure to almost dryness and the residue was extracted warm benzene (3×2 ml). The benzene extract was concentrated to a volume of 2 ml and then diluted with 8 ml of petroleum ether to induce precipitation. The solid precipitate was collected by filtration, dried in vacuum to afford 31 mg of the title compound as a white solid, mp 130°-141° (dec).

IR(KBr): 3400 (OH and NH), 1730 (lactone and ketone C=O), 1640 (amide C=O), 1450, 1375 (sulfate), 1190 (sulfate), 1085, 985 cm$^{-1}$.

1H NMR (CDCl$_3$, 400 MHz): 9.03 (d, J=13 cps, 2H, protons c), 8.47 (m, 1H, proton b), 8.01 (m, 2H, protons a).

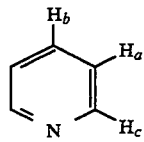

3.41 (d), 3.30 (d), 3.14 (s) (all 3H, —OCH$_3$) ppm.
MS (neg. ion FAB): 1008 (M−), 929.

EXAMPLE 7

Rapamycin 42-ester with carbamic acid

A solution of 2.0 g of rapamycin in 10 ml of dichloromethane and 2 mL of dry pyridine was cooled to −78° C. under a nitrogen atmosphere. To this solution, 662 mg 4-nitrophenyl chloroformate was added; the resulting solution was stirred at room temperature under nitrogen for 20 hours. The mixture was diluted with water and extracted with dichloromethane. The dichloromethane extract was washed with water, dried over MgSO$_4$ and evaporated. The residue was chromatographed on silica gel. Elution with 33% ethyl acetate in n-hexane gave 2.07 g of rapamycin 42-p-nitrophenyl carbonate as a white foam.

A solution of 630 mg rapamycin 42-p-nitrophenyl carbonate in 25 mL dichloromethane was treated at 0° with ammonia gas for one hour. The resulting yellow suspension was filtered and the flitrate was evaporated. The residue was chromatographed on silica gel. Elution with 25% n-hexane in ethyl acetate afforded 430 mg of the title compound as a white foam, mp 101°-103°.

IR(KBr): 3450 (OH and NH), 1720 (lactone and ketone C=O), 1645 (amide C=O), 1460, 1190, 890, 760 cm$^{-1}$. $^1$H NMR (CDCl$_3$, 400 MHz): δ 4.6 (s, 2H, NH$_2$), 3.40, 3.33, 3.14 (all s, 3H, —OCH$_3$) ppm. MS (neg. ion FAB): 956 (M−), 590, 364.

EXAMPLE 8

Rapamycin 27-oxime, 42-ester with carbamic acid

A solution of 320 mg rapamycin 42-ester with carbamic acid in 10 ml methanol was treated at room temperature with 120 mg sodium acetate and 100 mg hydroxylamine hydrochloride. The mixture was stirred at room temperature under nitrogen for 4 hours, diluted with water and extracted with ethyl acetate. The extract was washed, dried with MgSO$_4$ and evaporated. The residue was chromatographed on silica gel. Elution with ethyl acetate/n-hexane (3/2) afforded 245 mg of the title compound as a white solid, mp 114°-117°.

IR (KBr): 3430 (OH and NH), 1725 (lactone and ketone C=O), 1635 (amide C=O), 1455, 1090, 990 and 740 cm$^{-1}$. $^1$NMR (CDCl$_3$, 400 MHz):

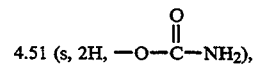

3.39 (s, 3H, OCH$_3$) ppm. MS (neg ion FAB): 972 (M−), 590.

EXAMPLE 9

Rapamycin 42-ester with 8-quinolinesulfonic acid

A solution of (0.30 g, 0.33 mmol) rapamycin and (0.29 g, 1.28 mmol) 8-quinolinesulfonyl chloride in 5 mL pyridine was stirred at 20° C. for 24 hours. The reaction mixture was partitioned between 2N HCl (10 mL) and ethyl acetate. The organic layer was washed with brine, dried over MgSO$_4$, stripped of solvent and chromatographed on silica gel eluted with 30% ethyl acetate in methylene chloride, affording 130 mg of title compound as a white solid, mp 120°-165° C.

IR (KBr): 3430, 2925, 1715, 1640, 1170, 985 and 785 cm$^{-1}$.

NMR (CDCl$_3$, 400 MHz): δ 9.18 (1H), 8.49 (1H), 8.25 (1H), 8.09 (1H), 7.65 (1H), 7.55 (1H), 3.32 (s, 3H, OCH$_3$), 3.13 (s, 3H, OCH$_3$), 2.60 (s, 3H, OCH$_3$).

MS (neg. FAB): 1104 (M−), 912, 590, 208.

EXAMPLE 10

Rapamycin 27-oxime, 42-ester with 8-quinolinesulfonic acid

Hydroxylamine hydrochloride (100 mg, 1.44 mmole) and sodium acetate (120 mg, 1.46 mmole) were added at 20° to a solution of 500 mg (0.45 mmole) rapamycin 42-ester with 8-quinolinesulfonic acid in 15 mL methanol and the reaction mixture was stirred 6 hours. The methanol was removed at reduced pressure and the residue partitioned between water and ethyl acetate. The organic portion was dried over MgSO$_4$, stripped to a solid foam and flash chromatographed through silica gel using a gradient of methanol of 1.3% to 2.0% in dichloromethane, yielding 170 mg of the title compound as a mixture of E and Z isomers, mp 121°-132° C.

IR (KBr): 3430, 2925, 1720, 1620, 1460, 1173, 984, 962 cm$^{-1}$. $^1$H NMR (CDCl$_3$ 400, MHz): resonances doubled by E/Z isomers): δ 9.19 (d, 1H, aromatic), 3.30, 3.29 (s,s; 3H, OCH$_3$), 3.17, 3.14 (s,s; 3H, OCH$_3$); 2.65, 2.63 (s,s; 3H, OCH$_3$. MS (neg ion FAB): 1119 (M−), 927, 590, 208.

EXAMPLE 11

Rapamycin (E)-27-O-(methyl)oxime, 42-ester with 8-quinolinesulfonic acid and

EXAMPLE 12

Rapamycin (Z)-27-O-(methyl)oxime, 42-ester with 8-quinolinesulfonic acid

To a solution of 820 mg (0.74 mmole) rapamycin 42-ester with 8-quinolinesulfonic acid in 15 mL methanol were added 0.16 g (1.9 mmole) sodium acetate and 0.16 g (1.9 mmole) methoxyamine hydrochloride at 20° C. After stirring 17 hours the reaction mixture was diluted with water and extracted into ethyl acetate, which was washed with brine, dried over $MgSO_4$ and evaporated to a white solid foam. Flash chromatography through silica gel yielded the Z isomer as a white solid, mp 119°–125° C.

IR (KBr): 3420, 2920, 1750, 1620, 1450, 1350 and 1170 $cm^{-1}$. NMR ($CDCl_3$, 400 MHz): δ 3.785 (s, 3H, $NOCH_3$); 3.29 (s, 3H, $OCH_3$), 3.16 (s, 3H, $OCH_3$), 2.66 (s, 3H, $OCH_3$). MS (neg ion FAB): m/z at 1133, 942, 590, 208. Further elution yielded the E isomer as a white solid, mp 122°–130° C. IR (KBr): 3420, 2930, 1735, 1645, 1455, 1350 and 1175 $cm^{-1}$. $^1$H NMR ($CDCl_3$, 400 MHz): δ 3.754 (s, 3H, $NOCH_3$), 3.28 (s, 3H, $OCH_3$), 3.13 (s, 311, $OCH_3$) and 2.61 (s, 3H, $OCH_3$). MS (neg ion FAB): m/z at 1133, 208.

The following compounds were prepared from methoxyamine hydrochloride, sodium acetate and the appropriate rapamycin 42-ester by employing the method previously described in Examples 11 and 12.

EXAMPLE 13

Rapamycin (Z)-27-O-(methyl)oxime, 42-ester with 4-nitrophenylcarbamic acid mp 138°–151° C.

EXAMPLE 14

Rapamycin (Z)-27-O-(methyl)oxime, 42-ester with 4-methylbenzenesulfonic acid mp 103°–115° C.

EXAMPLE 15

42-O-(1-Ethoxy-ethyl)-rapamycin

A mixture of 1.26 g (1.26 mmole) rapamycin 31-ester with N,N-dimethylglycine, 15 mg pyridinium p-toluenesulfonate and 1.7 mL ethyl vinyl ether in 20 mL dichloromethane was stirred at 20° C. under nitrogen in a closed container for 25 days, with additional quantities (same as above) of pyridinium p-toluenesulfonate and ethyl vinyl ether added on days 8 and 13. The reaction mixture was washed with water, dried over MgSO4 and stripped of solvent. Flash chromatography through silica gel using 1.0 to 1.5% methanol in dichloromethane provided 85 mg of the title compound as a white solid, mp 75°–82° C. IR (KBr): 3430, 2925, 1720, 1647, 1455, 1100 and 990 cm−1. NMR (300 MHz, CDCl3): d=4.87 (q, 1H [methine proton of ethoxyethyl]); 3.34 (s, 3H, $OCH_3$); 3.14 (s, 3H, $OCH_3$). MS (neg ion FAB): m/z at 985 (M−), 590.

EXAMPLE 16

42-O-(1-Ethoxy-ethyl)-rapamycin-(Z)-27-O-(methyl)oxime and

EXAMPLE 17

42-O-(1-Ethoxy-ethyl)-rapamycin-(E)-27-O-(methyl)oxime

To a solution of 300 mg 42-O-(1-ethoxy-ethyl)rapamycin in 20 mL methanol was added 110 mg methoxylamine hydrochloride and 100 mg sodium acetate. After stirring at ambient for 48 hours, the methanol was removed under reduced pressure and the residue was partitioned between water and ethyl acetate. The organic portion was washed with brine, dried over $MgSO_4$ and evaporated to dryness. Flash chromatography through silica gel using 1.25% methanol in dichloromethane yielded 80 mg of the Z isomer as a white solid, mp 99°–105° C. IR (KBr): 3435, 2935, 1750, 1650, 1455, 1195 and 890 $cm^{-1}$, NMR ($CDCl_3$, 400 MHz): d 3.81 (s, 3H, $NOCH_3$); 3.30 (s, 3H, $OCH_3$); 3.12 (s, 3H, $OCH_3$). MS (neg ion FAB): m/z at 1014, 590. Further elution yielded tile E isomer as a white solid, mp 95°–99° C. IR (KBr): 3440, 2940, 1750, 1636, 1455, 1200 and 890 $cm^{-1}$, MNR ($CDCl_3$, 400 MHz): d 3.84 (s, 3H, $NOCH_3$); 3.31 (s, 3H, $OCH_3$); 3.17 (s, 3H, $OCH_3$). MS (neg ion FAB): 1014, 590).

EXAMPLE 18

Rapamycin (Z)-27-O-(methyl)oxime-42-ester with butylcarbamic acid

To a solution of rapamycin (Z)-27-O-methyl-oxime, 42-carbonate with 42-O-4-nitrophenoxycarboxylic acid (0.47 g, 0.425 mmol) in dichloromethane (25 mL) at 0° C. was added butylamine (0.095 mL, 0.961 mmol) dropwise. The reaction was warmed to room temperature and stirred for 48 h. The reaction was then quenched with 25 mL $H_2O$. The organic layer was separated, and the aqueous layer extracted three times with EtOAc. The combined organic layers were washed with brine and dried over $Na_2SO_4$. The solution was filtered and concentrated in vacuo to afford a pale yellow foam. TLC analysis (25% EtOAc/hexane) indicated one major component. The reaction mixture was dissolved in EtOAc (15 mL) and the compounds separated by flash chromatography (silica gel on a 50 mm column, 30% EtOAc - hexane). The compound was concentrated in vacuo to afford the title compound as a pale yellow foam (0.229 g, 48.7% yield). $^1$H NMR (400 MHz, DMSO-$d_6$): δ 7.05 (m, 1H), 4.3–4.4 (m, 1H), 3.75 (s, 3H). MS (neg. ion FAB) m/e: 1041.5 [M−], 590.3, 546.3. Anal. calcd. for $C_{57}H_{91}N_3O_{14} \cdot H_2O$: C 64.59%, H 8.78%, N 3.97%; Found: C 64.08%, H 8.59%, N 4.00%. IR (KBr, $cm^{-1}$): 3400, 2960, 1725, 1640, 1530, 1450.

What is claimed is:

1. A compound of the structure

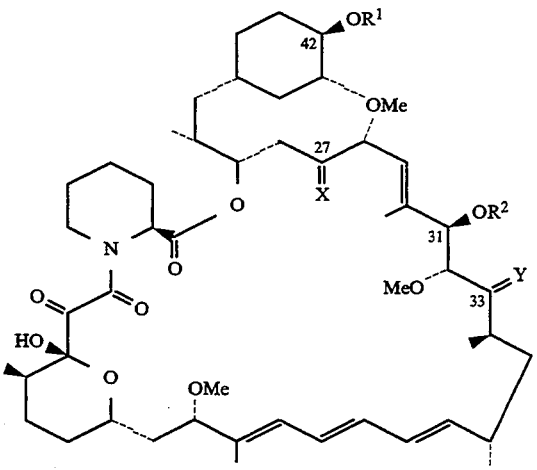

wherein $R^1$ and $R^2$ are each, independently, hydrogen, —CONH$_a$—{{(CR$^3$R$^4$)$_m$(—A—(CR$^5$R$^6$)$_n$)$_p$}$_q$—B}$_r$; —SO$_2$R$^7$; —SO$_3$H; —CHR$^8$O(CH$_2$)$_t$R$^9$; or

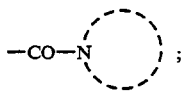

$R^3$, $R^4$, $R^5$, $R^6$, and B are each, independently, hydrogen, alkyl of 1-6 carbon atoms, alkenyl of 2-7 carbon atoms, alkynyl of 2-7 carbon atoms, hydroxyalkyl of 1-6 carbon atoms, alkoxyalkyl of 2-12 carbon atoms, alkylthioalkyl of 2-12 carbon atoms, alkylaminoalkyl of 2-12 carbon atoms, dialkylaminoalkyl of 3-12 carbon atoms, arylalkyl of 7-10 carbon atoms, cycloalkyl of 3-8 carbon atoms, —OR$^{10}$, —SR$^{10}$, halogen, —CN, —NO$_2$, —CF$_3$, —COR$^{10}$, —CO$_2$R$^{10}$, —CONHR$^{10}$, —SO$_2$R$^{10}$, —OSO$_3$R$^{10}$, —NR$^{10}$R$^{11}$, —NHCOR$^{10}$, —NHSO$_2$R$^{10}$, or Ar;

X is =NOR$^{12}$ or =NNR$^{12}$R$^{13}$;

Y is O, =NOR$^{12}$, or =NNR$^{12}$R$^{13}$;

$R^7$, $R^{12}$, and $R^{13}$ are each, independently, hydrogen, alkyl of 1-6 carbon atoms, alkenyl of 2-7 carbon atoms, alkynyl of 2-7 carbon atoms, arylalkyl of 7-10 carbon atoms, or Ar;

$R^8$, $R^9$, $R^{10}$, and $R^{11}$ are each, independently, hydrogen, alkyl of 1-6 carbon atoms, arylalkyl of 7-10 carbon atoms, alkenyl of 2-7 carbon atoms, alkynyl of 2-7 carbon atoms, hydroxyalkyl of 1-6 carbon atoms, alkoxyalkyl of 2-12 carbon atoms, alkylthioalkyl of 2-12 carbon atoms, alkylaminoalkyl of 2-12 carbon atoms, dialkylaminoalkyl of 3-12 carbon atoms, cycloalkyl of 3-8 carbon atoms, or Ar;

A is —CH$_2$—, —NR$^{10}$—, —O—, —S—, —SO—, —SO$_2$—, —PR$^{10}$—, —CO—, —NHCO—, —NHSO—, or —P(O)(R$^{10}$)—;

Ar is aryl which may be optionally mono-, di-, or trisubstituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H;

is a nitrogen containing heterocyclic radical selected from the group consisting of pyridyl, pyrazinyl, piperidinyl, morpholinyl, piperazinyl, pyrrolidinyl, thiazolyl, pyrimidinyl, isoxazolyl, pyrrolidinyl, and imidazolyl that may be optionally mono-, di-, or tri-substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H;

a=0-1;
m=0-6;
n=0-6;
p=0-1;
q=0-1;
r=1-2; and
t=1-4;

wherein $R^3$, $R^4$, $R^5$, $R^6$, A, B, m, n, p, and q are independent in each of the —CON—{{(CR$^3$R$^4$)$_m$(—A—(CR$^5$R$^6$)$_n$)$_p$}$_q$—B}$_r$ subunits when r=2;

with the proviso that $R^1$ and $R^2$ are not both hydrogen, and further provided that if r=2, then a=0, and if r=1, then a=1;

or a pharmaceutically acceptable salt thereof.

2. The compound of claim 1 wherein Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, benzopyranyl, benz[b]-thiophenolyl, benzimidazolyl, benzthiazolyl, benzodioxolyl, piperidyl, morpholinyl, piperazinyl, tetrahydrofuranyl, or pyrrolidinyl or a pharmaceutically acceptable salt thereof.

3. The compound of claim 1 wherein X is =NOR$^{12}$ and Y is O or a pharmaceutically acceptable salt thereof.

4. The compound of claim 3 wherein $R^1$ is —CONH$_a$—{{(CR$^3$R$^4$)$_m$(—A—(CR$^5$R$^6$)$_n$)$_p$}$_q$—B}$_r$, r=1, a=1, and $R^2$ is hydrogen or a pharmaceutically acceptable salt thereof.

5. The compound of claim 4 wherein q=0 or a pharmaceutically acceptable salt thereof.

6. The compound of claim 5 wherein B is Ar or OR$^{10}$ or a pharmaceutically acceptable salt thereof.

7. The compound of claim 6 wherein Ar is phenyl or pyridyl or a pharmaceutically acceptable salt thereof.

8. The compound of claim 3 wherein $R^1$ is —SO$_2$R$^7$, and $R^2$ is hydrogen or a pharmaceutically acceptable salt thereof.

9. The compound of claim 8 wherein $R^7$ is Ar or a pharmaceutically acceptable salt thereof.

10. The compound of claim 1 which is rapamycin 27-oxime, 42-ester with 2-(pyridin-2-yl)-ethyl-carbamic acid or a pharmaceutically acceptable salt thereof.

11. The compound of claim 1 which is rapamycin 27-oxime, 42-ester with 2-hydroxyethyl carbamic acid or a pharmaceutically acceptable salt thereof.

12. The compound of claim 1 which is rapamycin 27-oxime, 42-sulfate ester pyridine salt.

13. The compound of claim 1 which is rapamycin 27-oxime, 42-ester with carbamic acid or a pharmaceutically acceptable salt thereof.

14. The compound of claim 1 which is rapamycin 27-oxime, 42-ester with 8-quinolinesulfonic acid or a pharmaceutically acceptable salt thereof.

15. The compound of claim 1 which is rapamycin (E)-27-O-(methyl)oxime, 42-ester with 8-quinolinesulfonic acid or a pharmaceutically acceptable salt thereof.

16. The compound of claim 1 which is rapamycin (Z)-27-O-(methyl)oxime, 42-ester with 8-quinolinesulfonic acid or a pharmaceutically acceptable salt thereof.

17. The compound of claim t which is rapamycin (Z)-27-O-(methyl)oxime, 42-ester with 4-nitrophenylcarbamic acid or a pharmaceutically acceptable salt thereof.

18. The compound of claim 1 which is rapamycin (Z)-27-O-(methyl)oxime, 42-ester with 4-methylbenzenesulfonic acid or a pharmaceutically acceptable salt thereof.

19. The compound of claim 1 which is 42-O-(1-ethoxy-ethyl)-rapamycin-(Z)-27-O-(methyl)oxime or a pharmaceutically acceptable salt thereof.

20. The compound of claim 1 which is 42-O-(1-ethoxy-ethyl)-rapamycin-(E)-27-O(methyl)oxime or a pharmaceutically acceptable salt thereof.

21. The compound of claim 1 which is rapamycin (Z)-27-O-(methyl)oxime, 42-ester with butylcarbamic acid or a pharmaceutically acceptable salt thereof.

* * * * *